United States Patent [19]
Hellenbrand

[11] 3,985,121
[45] Oct. 12, 1976

[54] HEART DETECTIVE

[75] Inventor: Samuel H. Hellenbrand, New York, N.Y.

[73] Assignee: International Telephone and Telegraph Corporation, Nutley, N.J.

[22] Filed: May 20, 1975

[21] Appl. No.: 579,103

[52] U.S. Cl. .................................. 128/2 K; 35/17; 128/2.05 S
[51] Int. Cl.² ........................................ A61B 5/02
[58] Field of Search ............... 128/2 K, 2 R, 2.05 S, 128/2.06 A; 35/17; 324/77

[56] References Cited
UNITED STATES PATENTS

| | | | |
|---|---|---|---|
| 3,416,081 | 12/1968 | Gutleber | 324/77 |
| 3,665,087 | 5/1972 | Poylo | 35/17 |
| 3,769,526 | 10/1973 | Krause | 35/17 X |
| 3,789,159 | 1/1974 | Feit et al. | 128/2.06 A X |
| 3,797,129 | 3/1974 | Ravin et al. | 35/17 |

*Primary Examiner*—William H. Grieb
*Attorney, Agent, or Firm*—Paul W. Hemminger; John T. O'Halloran

[57] ABSTRACT

The heart detective described is a portable device for detecting and indicating when heart sounds emanating directly from a physical area under auscultation are representative of a heart disorder. The device detects the audio sounds emanating from the classical four physical areas of auscultation and compares these detected sounds to prerecorded sounds of the same areas representing a known heart disorder. A comparison is made between the detected sounds and the prerecorded sounds, and the correlations are indicated in a display on the device so that a determination may be made if the heart disorder is present. The device also contains means for accepting an auxiliary transducer for detecting heartbeat pulses and indicating the pulse rate.

8 Claims, 4 Drawing Figures

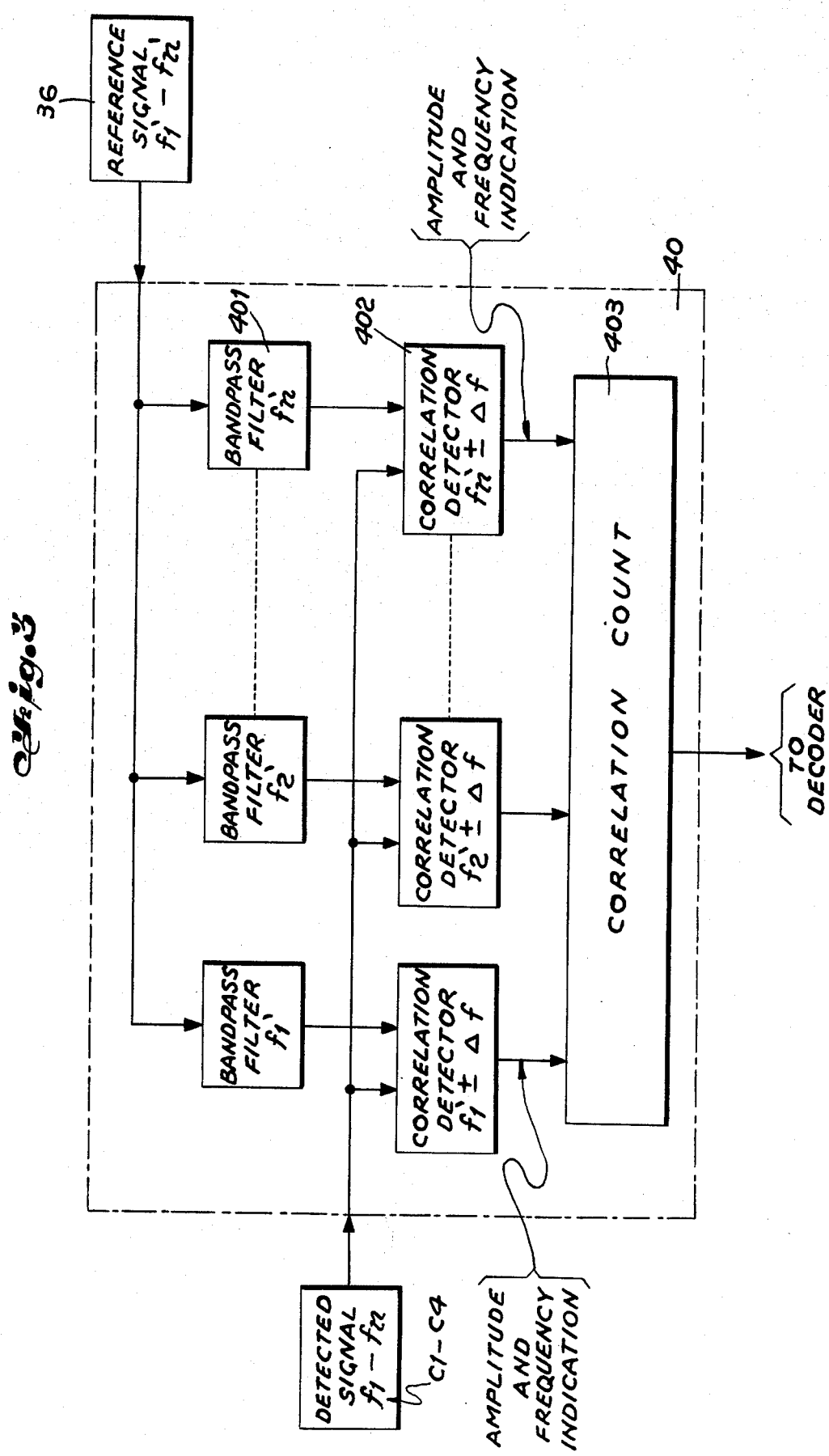

HEART DETECTIVE

BACKGROUND OF THE INVENTION

In general, this case relates to a method and apparatus for detecting and indicating when heart sounds emanating from particular physical areas of a person are indicative of a known heart disorder. More particularly, the invention intends to provide a means and method of detecting and comparing audio signals emanating from the classical four physical areas of auscultation with corresponding prerecorded audio signals representing various known heart disorders.

In U.S. Pat. No. 3,665,087, assigned to the assignee of the present invention, a manikin audio system was described in which proper placement of a synthetoscope on one of the four classical areas to be examined caused one of four audio signals stored on a continuous tape to be coupled to the ears of the examiner. This system has proven to be an extremely effective teaching tool, and although the audio signals do not emanate directly from the physical area under auscultation, the proper sounds in each of the four areas are coupled to the examiner at the time the particular region of the manikin is explored. There are 50 different heart disorders or diseases presently available for selection from the tape library, each tape representing one disease and having four audio tracks corresponding to the four areas. This enables the examiner to listen to the sounds for each disorder and learn at an individual pace the variations between sounds in the four areas.

The four classical sounds are related to the construction of the interior of the heart which is divided into four chambers, namely, the right antrum, right ventricle, left ventricle and left antrum. The right and left ventricles consist of several layers of muscle which serve as the primary pumps of the heart, and the left and right antrums serve as the receptacles for blood returning to the heart. Each of the four chambers produces a unique heart sound frequency spectrum that can be analyzed to indicate a disorder or malfunction of an associated chamber.

The manikin audio system is particularly adapted to be utilized as a teaching tool, and its use has been limited to medical students and those specializing in heart disorders. Therefore, a large library of information containing some fifty known heart disorders has not been available for use by a large majority due to limited access and availability at only a few teaching institutions. In addition, students, other than heart specialists, once they have left the teaching institutions and have been in practice for a number of years, soon lose the discrimination required for the various sounds for a given disease when exploring particular regions of the heart. Accordingly, a real need exists for a portable device, namely, a heart detective, which could utilize this known information during a physical examination and give an indication of a disorder to physicians or other trained personnel in this country, as well as in underdeveloped countries where doctors and heart specialists are in great demand. The device is not intended to be a definitive diagnosis, but rather to indicate a connection between a known disorder and the particular person being examined. Once a problem has been detected, a more thorough examination may be undertaken by a skilled heart diagnostician utilizing some of the more advanced electronic and computer analysis equipment. The device of the invention is particularly suited for use in remote areas and locations that do not have ready access to heart specialists and expensive analysis equipment.

SUMMARY OF THE INVENTION

It is therefore an object of the present invention to provide a method and means for indicating heart disorders.

Another object of the invention is to provide a portable device which may be used to detect and display when heart sounds emanating from areas of auscultation are indicative of a known heart disorder.

A still further object of the invention is to provide a means and method for comparing audio signals emanating in real time from the classical four physical areas of auscultation with prerecorded audio signals representing the same areas for a known disorder.

According to the broader aspects of the invention, a portable heart detective device is provided comprising means for simultaneously ascultating a plurality of areas and temporarily storing the detected heart sounds, means for comparing prerecorded heart sounds from said areas with the detected sounds, and means for displaying an indication of the correlation between the detected and recorded sounds.

A feature of the invention is that the portable device includes means to receive a transducer to detect heartbeat pulses and means to display the pulse rate.

BRIEF DESCRIPTION OF THE DRAWINGS

Other advantages and features of the invention will be readily appreciated by reading the following description in connection with the drawings, in which:

FIG. 3 shows, in block diagram form, a signal comparator for use in the embodiment of FIG. 2.

DESCRIPTION OF THE PREFERRED EMBODIMENT

The audio heart detective according to the present invention, is intended to be used with prerecorded tapes as disclosed in U.S. Pat. Nos. 3,789,159 and 3,769,526. One tape normally represents one disease and contains four tracks recorded in predetermined synchronism to represent the four classical areas of auscultation which are examined for determining whether or not a problem exists. A track or channel on the tape contains synchronization information and the information is in the form of either a foil strip or a 5 kHz synchronizing pulse. The synchronization information is located 5 seconds apart and corresponds to a breath cycle of approximately five heart sounds per cycle. Each of the four tracks or channels contains this information which has been recorded as in the above patents.

The device of the invention is designed to detect the heart sounds in real time from the four classical areas so that they may be compared channel by channel with the stored information on a tape and determine if there is any correlation between the detected signals and the recorded signals. The energy spectrum of the human heart varies, but normally can be plotted as intensity versus time in the range of 20 to 600 Hz. The device and method of the invention is designed to utilize this vast store of recorded acoustical information for each heart sound for some 50 diseases by feeding the detected audio signals to a signal comparator which is able to compare channel by channel the information on a given tape track to the information obtained and stored in real time.

Figure 1A:
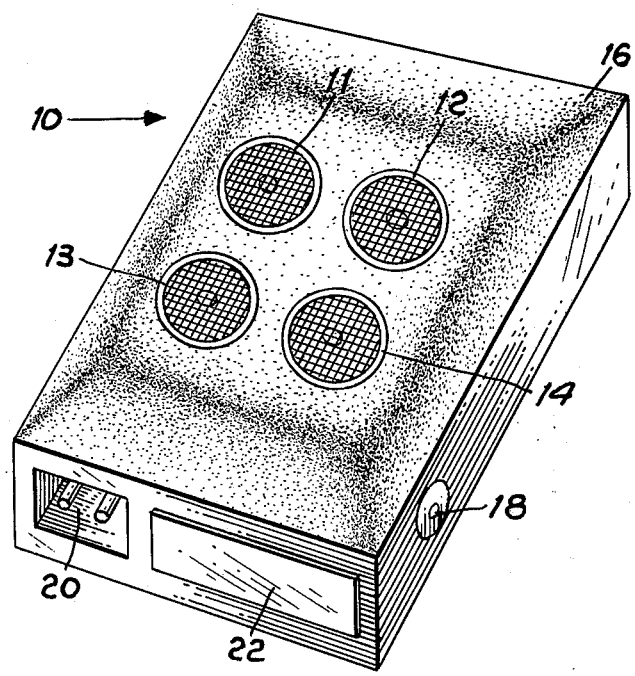
FIGS. 1A and 1B are a perspective illustration of a portable heart detective device according to the invention.
Figure 1B:
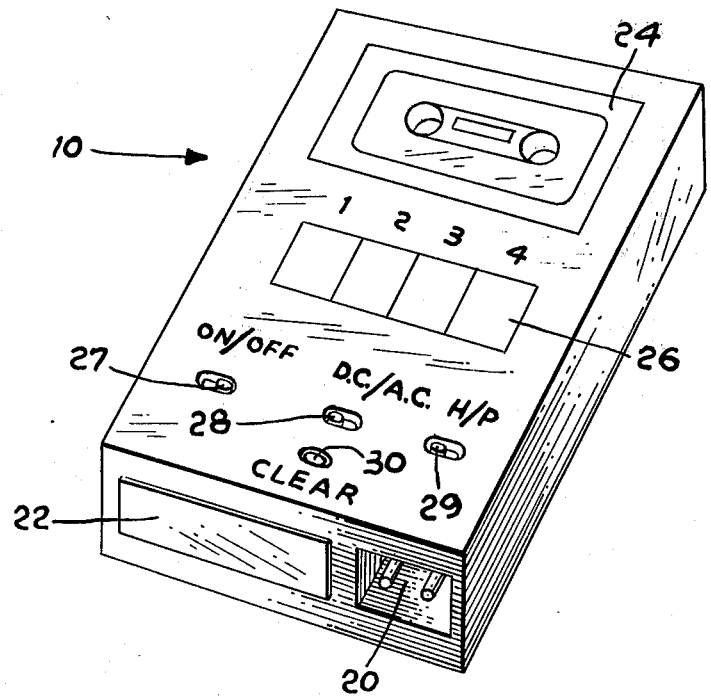

Referring now to FIGS. 1A and 1B, the portable device according to the information will be described. The heart detective 10 is a portable device having on one side four directional microphones 11, 12, 13, 14 positioned within a styrofoam or other isolating material 16 which may be covered by a vinyl coating. The microphones are positioned according to the four classical areas of examination of the human heart. The portable device is approximately the size of a tape recorder and may be handheld against the chest of the person under examination. A jack receptacle 18 is provided for insertion of a connector for an auxiliary pulse detecting transducer. The device will display pulse rate when it is set in a pulse monitoring mode. The device contains a receptacle 20 for coupling AC power and DC battery location 22 to enable battery operation of the device for areas where AC connection is not possible or impractical.

As illustrated in FIG. 1B, the side opposite the microphones has the means 24 for receiving and reading a tape cartridge having recorded thereon the reference signals for a particular disorder. Below the tape insertion area is a display panel 26 which may be an LED display. The display 26 will provide four discrete indications corresponding to the four detected audio signals. Each channel display numbered 1, 2, 3, 4 provides an indication of the correlation of a predetermined number of specific spectral quantities. The display may be numerical, indicating a number which can then be used with a reference table, or provide a "yes," "no," "go," "no-go" indication for each of the detected acoustical sounds. Below the display 26 is an on-off switch 27, a DC-AC mode switch 28, a heart or pulse mode switch 29, and clear button 30. When switch 29 is in the pulse mode, the display 26 will indicate pulse rate. The pulse rate, of course, will only be displayed when a pressure sensitive transducer has been coupled to the device.

Figure 2:
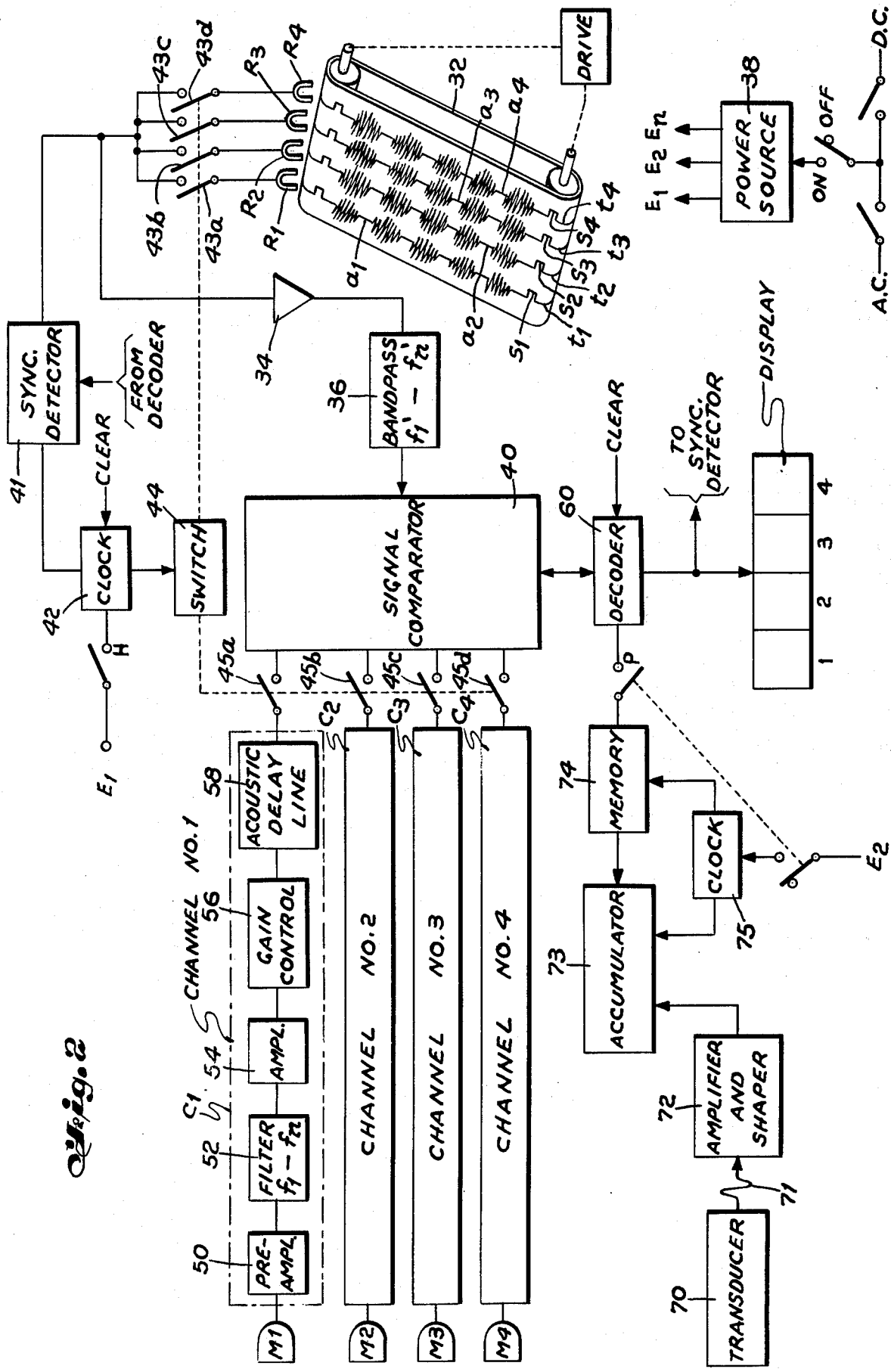
FIG. 2 shows, in block diagram form, a preferred embodiment constructed in accordance with the principles of the invention.

FIG. 2 shows, in block diagram form, an embodiment of the invention. A single continuous prerecorded tape 32 is shown, each track $t_1$, $t_2$, $t_3$, $t_4$ of each tape carrying the audio signals $a_1$ to $a_4$ corresponding to the audio sounds for the four classical areas of auscultation for one heart disorder. The 5 kHz synchronizing pulses $s_1$ to $s_4$ are indicated for each cycle. For a small portable device according to this embodiment, each tape 32 or tape cassette will contain audio reference signals for one disease, and it should be understood that in more elaborate schemes that a plurality of prerecorded diseases may be included with larger tapes and tape drive, including the appropriate clocking and disease select means. However, it must be understood that the device is designed for portable field use to provide an indication of a problem and one or more of the major heart diseases are easily handled by changing cassettes.

Each of the prerecorded audio signals $a_1$ to $a_4$ include the spectral reference frequencies $f_1'$ to $f_n'$ which are to be used by the signal comparator to determine a correlation between the detected and the recorded signals. The plurality of reading heads $R_1$ to $R_4$ selectably read the signals $a_1$ to $a_4$ and couple them to driver amplifier 34 and through bandpass filter 36 having a band spectrum $f_1'$ to $f_n'$ corresponding to the specific spectral lines to be used as a reference. The output from the filter 36 is coupled to the signal comparator 40 as to be further described in connection with FIG. 3.

With a cassette in position, the power supply 38 turned on, and the device placed in the H or heart mode, the components are initialized. Clock 42 will switch means 44 to a first operative condition to latch one of the contact means 43a to 43d and one corresponding contact 45a to 45d to the closed condition. Although the switch means 44 is shown connected by dashed lines to contacts 43 and 45, it should be appreciated that the implementation will be with transistor switching circuits. Switch 44 when clocked will sequentially switch contacts 45a – 45d to enable the real time audio signals from channels C1 to C4 to be coupled to the signal comparator 40. The comparator 40 will correlate the acoustical sounds received in real time from the microphones M1 to M4 and sounds $a_1$ to $a_4$ recorded on an associated track $t_1 - t_4$ of the tape 32. The reference and detected audio signals will be selectively coupled to the signal comparator 40 according to the clocking of switch 44, so that the associated input channels and references are coupled to the signal comparator. Coupled to each directive microphone M1 – M4 is an audio channel containing a preamplifier 50, a filter 52 having a bandpass corresponding to the reference spectrum, the output of the filter being coupled to an amplifier 54 with gain control means 56 to standardize the level of signal intensity, and an acoustic delay line memory 58. The acoustic delay memory may, for example, be a magnetostrictive delay line in the form of a closed loop which is adapted to temporarily store the acoustic real time signals for each channel and couple them to the signal comparator 40.

One type of signal comparator 40 is described in connection with FIG. 3 and will produce a correlation output which is coupled to the decoder 60 which decodes the output into a display sequence to indicate for each channel the correlation figure. Displays 1, 2, 3, 4 will then indicate the correlation between channels C1 to C4 and reference tracks $t_1 - t_4$. A zero may represent insufficient correlation or a reference table may be used with a correlation number from 0 – 9 for each channel. The components are cleared by activating the clear button on the device. The output from the decoder 60 also enables synchronization detector 41 which detects a synchronization signal $s_1$ and activates the clock to a second output to clock switch means 44, to switch channels so that the four channels may be sequentially compared.

The heartbeat pulses may be checked by switching the device to the pulse mode P. In this mode, the audio components are disconnected and the pulse rate components are connected to the decoder and display. A pressure sensitive transducer 70 is coupled by connector cable 71 and detects the R waves. The detected pulses are coupled to an amplifier and shaper 72 whose output is counted and accumulated in accumulator 73. The accumulator feeds a memory 74 under the control of a clock 75. The accumulator 73 is normally cycled in one minute as is the clocked memory which couples the pulse count to the decoder 60 for display in positions 2, 3 and 4. The readout is the pulse rate per minute. In each ensuing minute, the memory will retain the previous accumulated count until a new count is coupled to the memory and which, in turn, couples the subsequent counts to the decoder for display.

Referring now to FIG. 3, one type correlator for use as the signal comparator of FIG. 2 is illustrated. It should be noted that sounds emanating from the heart generally fall within two ranges, those sounds which are below 20 cycles and are attributable to gross movements of the chest wall and those sounds in the range of 20 to 600 Hz which are audible and generally associated with cardiac auscultation. It has further been found that 95% of the heart sound energy lies below 100 Hz so that the bandpass filters may be limited, if desired, and cover 95% of all the heart sounds. It is recognized that certain disorders have frequency spectral lines above 100 Hz and these may be included if within desired size and weight parameters for the comparator. The signal comparator proposed in the preferred embodiment of the invention is a spectrum analyzer which makes use of cross-correlation filters to effect narrow banding, the cross-correlation filters acting to establish the presence of a particular frequency $f \pm \Delta f$ frequency and, in addition, the amplitude of the specific spectral line. One such analyzer utilizing the correlation detectors which is proposed for utilization in the instant invention, is described in U.S. Pat. No. 3,416,081, issued Dec. 10, 1968 and assigned to the assignee of the instant invention. Insofar as this patent is necessary for an understanding of the instant invention, it is hereby incorporated by reference. The spectrum analyzer of FIG. 3 is used to analyze the frequency spectrum of the complex detected heart signal and to do so under very poor signal-to-noise ratios. The analyzer is adaptable to any desired degree of resolution which can be obtained by suitable adjustment of the parameters of the analyzer.

The reference signals $f_1'$ to $f_n'$ from each track of the tape recorder will be coupled to a plurality of bandpass filters 401, each filter passing one of the reference parameters $f_1', f_2', f_n'$. For example, if it is desired to analyze the frequencies from 20 Hz to 100 Hz, nine bandpass filters 401 may be utilized with each filter centered at 10 Hz intervals. The input signal selectively coupled from channels C1 – C4 contains the real time audio heart signal having a frequency spectrum $f_1$ to $f_n$. The signal is coupled with the outputs from filters $f_1'$, $f_2', f_n'$ to the correlation detectors 402. The correlation detectors 402 will produce an amplitude and frequency indication which is a measure of the amplitude and frequency $f_1' \pm \Delta f$, $f_2' \pm \Delta f$ and $f_n' \pm \Delta f$. By simply monitoring with a correlation counter 403, the outputs from the detectors 402 can easily count the number of amplitudes and frequencies within $\pm \Delta f$ of the input spectrum. The correlation count is then coupled to the decoder of FIG. 2 and the number of correlations displayed in appropriate locations. The output from the decoder will then trigger the synchronization detector 41 to enable switching another real time signal to the comparator while simultaneously coupling the associated reference signal to the comparator. The cross-correlation is then made as to the audio heart sounds for this second channel and the indication displayed. This cycle is repeated for each of the four channels so that for one heart disease, the four channel correlation count will indicate to the operator directly or with reference to a chart, whether or not a sufficient correlation has been made to indicate a known disorder in the examined individual.

The disclosed method of detecting sounds from a human heart for the four classical areas generally associated with cardiac auscultation, comparing them with the frequency spectrum for known diseases, and correlating the two sounds to produce a correlation indication will, within acceptable tolerances, identify a cardiac problem in the examined person.

The heart detective device of the instant application will find ready use by most physicians, both in urban and rural areas, to check their diagnosis and to determine whether or not any of their suspicions as to particular type malfunctions can be confirmed by obtaining a correlation indication with this portable device. The operation of this apparatus has been sufficiently simplified to enable semi-skilled technicians to utilize the device and with appropriate charts to determine if the correlation indication is sufficiently high as to warrant further investigation by a trained heart specialist with or without more complicated analysis equipment. The incorporation in this equipment of a pulse rate indicator will help to highlight problem areas since the pulse rate count characteristically varies with certain abnormalities of the heart and the appropriate comparison between the correlation indication and the pulse rate count can be meaningfully made.

While I have described above the principles of my invention in connection with specific apparatus, it is to be clearly understood that this description is made only by way of example and not as a limitation to the scope of my invention as set forth in the objects thereof and in the accompanying claims.

I claim:

1. A heart detective comprising in combination:
   means for simultaneously detecting a plurality of heart sounds, said detecting means includes a plurality of directive microphones and audio channels, each of said microphones coupling one of said plurality of detected heart sounds to an associated audio channel;
   means providing a plurality of prerecorded heart sounds, said prerecorded heart sounds are stored on a multitrack magnetic tape in a predetermined synchronism;
   means for comparing said detected heart sounds and said prerecorded heart sounds to produce a correlation indication, said comparing means includes a correlation detector providing an amplitude and frequency correlation indication between one of said detected heart sounds and one of said prerecorded heart sounds;
   means responsive to the predetermined synchronism to sequentially control the comparison of one of said plurality of detected heart sounds to a corresponding one of said prerecorded heart sounds; and
   means coupled to said comparing means for displaying said correlation indication for each of said plurality of heart sounds.

2. The combination of claim 1 including pulse beat detecting means and means coupled to said detecting means for displaying a pulse rate.

3. The combination of claim 1 wherein said display means includes a decoder and a numerical display location for each of said plurality of detected heart sounds.

4. The combination of claim 1 wherein each said audio channel includes
   a preamplifier,
   a predetermined bandpass filter, an amplifier and gain control means, and
acoustic delay means for temporarily storing and coupling the associated one of said detected heart sounds to said comparator.

5. The combination of claim 1 wherein said means providing includes at least one reading head for selectably coupling said plurality of prerecorded heart sounds to said comparator.

6. A method of examination for detecting when heart sounds emanating from particular areas are indicative of a heart disease, the method comprising:
   inserting a tape recording containing a plurality of recorded audio sounds corresponding to a known disease into a portable device;
   placing said device on the physical area under auscultation and simultaneously receiving a plurality of detected audio sounds;
   comparing said plurality of detected audio sounds with said recorded sounds; and
   displaying on said device a correlation indication between said recorded and detected sounds, whereby a predetermined number of correlations indicate said known disease.

7. The method of claim 6 including attaching a transducer to said portable device for recording pulse beats from a particular physical area, and displaying a pulse rate on the same display used for said correlation indication.

8. A portable heart detective device comprising in combination:
   four directive microphones arranged on one face of said device to correspond to the classical four physical areas of auscultation;
   four audio channels coupled in one-to-one correspondence to said microphones and responsive to detect audio signals emanating from the four areas, said channels including means for temporarily storing the detected audio signals;
   said device including means for receiving a prerecorded tape and producing therefrom four audio signals corresponding to the four areas for a particular condition;
   a signal comparator for comparing the four detected audio signals to the corresponding four prerecorded signals for said particular condition; and
   means for indicating on said device a correlation between a detected signal and a corresponding prerecorded signal for each of said four areas.

* * * * *